(12) United States Patent
Schoenfeldt et al.

(10) Patent No.: US 10,118,166 B2
(45) Date of Patent: Nov. 6, 2018

(54) ZEOLITIC MATERIALS WITH MODIFIED SURFACE COMPOSITION, CRYSTAL STRUCTURE, CRYSTAL SIZE, AND/OR POROSITY, METHODS FOR MAKING THE SAME, AND METHODS FOR CONVERTING OXYGENATES TO OLEFINS VIA REACTIONS CATALYZED BY THE SAME

(71) Applicant: UOP LLC, Des Plaines, IL (US)

(72) Inventors: Nick J. Schoenfeldt, Chicago, IL (US); David Stickley, Lombard, IL (US); Jaime G. Moscoso, Mt. Prospect, IL (US); Deng-Yang Jan, Elk Grove Village, IL (US); Benjamin Daniel Yuhas, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 516 days.

(21) Appl. No.: 14/519,441

(22) Filed: Oct. 21, 2014

(65) Prior Publication Data
US 2015/0352538 A1   Dec. 10, 2015

Related U.S. Application Data

(60) Provisional application No. 62/009,077, filed on Jun. 6, 2014.

(51) Int. Cl.
| | | |
|---|---|---|
| *B01J 29/85* | (2006.01) | |
| *C07C 1/20* | (2006.01) | |
| *C01B 39/54* | (2006.01) | |
| *B01J 29/06* | (2006.01) | |
| *C01B 37/08* | (2006.01) | |
| *C01B 39/02* | (2006.01) | |
| *B01J 35/02* | (2006.01) | |

(52) U.S. Cl.
CPC .............. *B01J 29/85* (2013.01); *B01J 29/06* (2013.01); *C01B 37/08* (2013.01); *C01B 39/026* (2013.01); *C01B 39/54* (2013.01); *C07C 1/20* (2013.01); *B01J 35/023* (2013.01); *B01J 2229/12* (2013.01); *B01J 2229/186* (2013.01); *B01J 2229/34* (2013.01); *B01J 2229/38* (2013.01); *C07C 2529/85* (2013.01); *Y02P 20/52* (2015.11); *Y02P 30/42* (2015.11)

(58) Field of Classification Search
None
See application file for complete search history.

(56) References Cited

U.S. PATENT DOCUMENTS

| | | | |
|---|---|---|---|
| 6,620,983 B1 | 9/2003 | Cao et al. | |
| 8,901,364 B2* | 12/2014 | Corma | B01J 29/06 |
| | | | 502/77 |
| 2003/0004056 A1* | 1/2003 | Mees | B01J 29/84 |
| | | | 502/208 |
| 2004/0217061 A1* | 11/2004 | Corzani | B01J 20/02 |
| | | | 210/660 |
| 2007/0267324 A1* | 11/2007 | Dalloro | B01J 29/088 |
| | | | 208/138 |
| 2011/0108459 A1* | 5/2011 | Simon | B01J 29/084 |
| | | | 208/89 |
| 2011/0295050 A1 | 12/2011 | Nesterenko et al. | |
| 2012/0159804 A1* | 6/2012 | Sauerbeck | A47L 15/0042 |
| | | | 34/353 |
| 2012/0165558 A1 | 6/2012 | Ryoo et al. | |
| 2012/0258852 A1* | 10/2012 | Martinez | B01J 29/041 |
| | | | 502/60 |
| 2013/0184147 A1 | 7/2013 | Ryoo et al. | |
| 2014/0326641 A1* | 11/2014 | Bonduelle | B01J 37/0236 |
| | | | 208/58 |

FOREIGN PATENT DOCUMENTS

| | | | |
|---|---|---|---|
| CN | 1686796 A | 10/2005 | |
| CN | 101121533 B | 5/2010 | |
| CN | 102658197 A | 9/2012 | |
| CN | 102923727 A | 2/2013 | |
| EP | 0161488 | * 11/1985 | |

OTHER PUBLICATIONS

Verboekend, Danny et al. Catal. Sci. Technol. 1, 879-890 (2011).*
Perez-Ramirez et al. "Tailored Mesoporosity Development in Zeolite Crystals by Partial Detemplation and Desilication". Adv. Funct. Mater. 164-172, 19 (2009).*
Groen, Johan et al. "Mechanism of Hierarchial Porosity Development in MFI Zeolites by Desilication: The Role of Aluminum as a Pore Directing Agent". Chem Eur J. 4983-4994, 11 (2005).*
Buchholz, A. et al. "Thermal Stability . . . NMR Spectroscopy. Microporous and Mesoporous Materials". 267-278, 56 (2002).*
Silaghi et al., Challenges on Molecular Aspects of Dealumination and Desilication of Zeolites, Microporous andMesoporous Materials 191 (2014) 82-96.
Fjermestad et al., Mechanistic Comparison of the Dealumination in SSZ-13 and the Desilication in SAPO-34, J. Phys. Chem. C 2013, 117, 13442-13451.
Liu et al., An Effective Modification Method to Improve the Catalytic Property of SAPO-34 in Methanol-to-Olefins Reactioin, Dalian Institute of Chemical Physics, Zhongshan Road 457, Dalian 116023, China.
Jun et al., A Facile Synthesis of SAPO-34 Molecular Sieves with Microwave Irradiation in Wide Reaction Conditions, Bull. Korean Chem. Soc. 2011, vol. 32, No. 6.

* cited by examiner

Primary Examiner — Sheng H Davis

(57) ABSTRACT

Zeolitic materials with modified surface composition, crystal structure, crystal or particle size, and/or porosity, methods for making the same, and methods for converting oxygenates to olefins using the same are provided herein. In an exemplary embodiment, a method for reducing a surface silicon content of a silicon-containing zeolitic material is provided that includes providing a silicon-containing zeolitic material; and contacting the silicon-containing zeolitic material with a modifying solution comprising one or more of an amine, an alcoholamine, and an amino acid. In this embodiment, the contacting occurs under conditions suitable for the modifying solution to reduce a surface silicon content, increase the porosity, and/or decrease an average crystal or particle size of the silicon-containing zeolitic material.

13 Claims, 1 Drawing Sheet

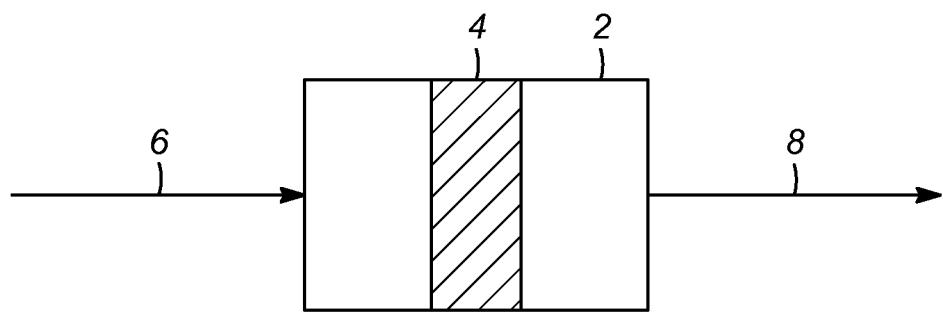

ZEOLITIC MATERIALS WITH MODIFIED SURFACE COMPOSITION, CRYSTAL STRUCTURE, CRYSTAL SIZE, AND/OR POROSITY, METHODS FOR MAKING THE SAME, AND METHODS FOR CONVERTING OXYGENATES TO OLEFINS VIA REACTIONS CATALYZED BY THE SAME

CROSS-REFERENCE TO RELATED APPLICATION

This application claims the benefit of U.S. Provisional Application No. 62/009,077, filed Jun. 6, 2014, which is hereby incorporated by reference in its entirety.

TECHNICAL FIELD

The technical field generally relates to crystalline molecular sieve catalysts and catalyst supports, methods for making the same, and methods for converting oxygenates to hydrocarbons using the same. More particularly, the technical field relates to zeolitic materials with modified surface composition, crystal structure, crystal or particle size, and/or porosity, methods for making the same, and methods for converting oxygenates to hydrocarbons using the same.

BACKGROUND

Crystalline molecular sieves are among the most important materials in industrial catalysts today. These materials, including aluminosilicate zeolites, metal-substituted aluminosilicate zeolites, silicoaluminophosphates (SAPOs), metal-substituted silicoaluminumphosphates (MeAPSOs), aluminophosphates (ALPOs), and metal-substituted aluminum phosphates (MeAPOs) are typically microporous materials with a defined pore structure that can accommodate a number of different cations. Molecular sieves find use in a variety of applications. For instance, aluminosilicate zeolites (in particular, synthetic zeolites), SAPOs and ALPOs are widely used as catalysts or catalyst support materials in the petrochemical industry, where they serve as catalysts or catalyst support materials for fluid catalytic cracking and hydrocracking.

Acid site density of a zeolitic material is determined by the chemical composition at a surface of the material defining a pore (e.g., the relative proportions of Me (substituted metals) (if present), silicon (Si) (if present), aluminum (Al), and phosphorous (P) (if present)). It is also known that acid site density affects catalytic performance. For example, it is known that light olefin selectivity during catalytic conversion of methanol to olefins with a SAPO catalyst can be improved by reduction of acid site density on a catalyst surface. Reduction of acid site density may be achieved in SAPO materials via reduction of the amount of silicon in the material. However, reduction of silicon in SAPOs prepared via conventional techniques is limited because as silicon content is reduced in the synthesis mixture, crystallization or formation of intergrowth of undesirable crystal structures (specifically, the crystal structure cotes denoted by AEI and/or AFI) into the otherwise chabazite (CHA) crystalline materials increases.

Additionally, catalytic behavior is affected by the pore size distribution of a zeolitic material. For instance, in a zeolitic material with a porous network comprising only micropores, catalytic activity is often limited by mass transfer, potentially limiting production rates and/or increasing the likelihood for undesirable secondary reactions.

Catalytic behavior is also affected by the crystal or particle size of a zeolitic material. For instance, catalytic activity is often limited by mass transfer in zeolitic materials with a porous network comprising relatively large particles or crystals, also potentially limiting production rates and/or increasing the likelihood for undesirable secondary reactions.

Accordingly, it is desirable to provide novel methods for making zeolitic materials with modified surface composition, crystal structure, crystal size, and/or porosity. Furthermore, other desirable features and characteristics will become apparent from the subsequent detailed description and the appended claims, taken in conjunction with the accompanying drawings and the foregoing technical field and background.

BRIEF SUMMARY

Silicon-containing zeolitic materials and methods for reducing a surface silicon content of a silicon-containing zeolitic material are provided herein. An exemplary method comprises the steps of: providing a zeolitic material comprising silicon at a surface of the zeolitic material; and contacting the surface of the zeolitic material with a modifying solution comprising one or more of an amine, an alcoholamine, or an amino acid. In this embodiment, contacting the surface of the zeolitic material with the modifying solution reduces an amount of silicon at the surface to generate a modified zeolitic material with reduced surface silicon content.

In other embodiments, compositions of matter are provided that comprise zeolitic materials having a pore structure comprising micropores. In one exemplary embodiment, a zeolitic material has a % porosity as measured by mercury porosimetry of about 65% to about 80%. In this exemplary embodiment, the zeolitic material comprises silicon at a first concentration within a depth of about 2 nm from a surface and a second concentration at a depth of about 40 nm or more from the surface, with the first concentration being about 0.9 to about 1.6 times the second concentration, such as about 1.2 to about 1.4 times the second concentration.

In another exemplary embodiment of a composition of matter, the zeolitic material has a % porosity as measured by mercury porosimetry of about 65% to about 80%; and comprises a crystalline material with an average crystal or particle size as measured by light scattering of about 400 nm to about 2500 nm size.

BRIEF DESCRIPTION OF THE DRAWINGS

The attached FIGURE (FIG. 1) is an illustration of a process flow of an exemplary apparatus and method for converting methanol to olefins via reaction catalyzed by an exemplary crystalline porous SAPO material with hierarchical pore structure as described herein.

DETAILED DESCRIPTION

The following detailed description is merely exemplary in nature and is not intended to limit the methods or apparatuses described herein. Furthermore, there is no intention to be bound by any theory presented in the preceding background or the following detailed description.

Zeolitic materials with modified surface composition, crystal structure, crystal or particle size, and/or porosity, methods for making the same, and methods for converting oxygenates to hydrocarbons and/or olefins using the same are provided herein. As used herein, the term zeolitic material should be understood to include aluminosilicate zeolites, metal-substituted aluminosilicate zeolites, silicoaluminophosphates (SAPOs), metal-substituted silicoaluminumphosphates (MeAPSOs), aluminophosphates (ALPOs), and metal-substituted aluminum phosphates (MeAPOs), with a defined pore structure comprising micropores, such as those materials conventionally used as catalysts or catalyst support materials. Metal-substituted zeolites, MAPSOs and MeAPOs, may be substituted with any element in groups 2 through 13 of the Periodic Table, with specific examples of suitable metals being magnesium (Mg), calcium (Ca), scandium (Sc), titanium (Ti), vanadium (V), chromium (Cr), manganese (Mn), iron (Fe), cobalt (Co), nickel (Ni), copper (Cu), zinc (Zn), and gallium (Ga). As used herein, "micropores" are pores with a maximum pore dimension, such as a pore diameter or length, of about 2 nm or less.

As used herein, modifying a surface composition of a zeolitic material includes modifying a surface composition such that an amount of one or more of silicon, aluminum, and/or phosphorous increases or decreases relative to an amount of one or more additional constituents. In some embodiments, the one or more additional constituents can be silicon, aluminum, and/or phosphorous. That is, in some embodiments, modifying a surface composition of a zeolitic material means modifying the ratio of silicon:aluminum:phosphorous (or a ratio of silicon:(aluminum+phosphorous)) at a surface of the material.

Further, the term "surface" is used to describe the region of a material bound by an upper surface of the material to a depth of at most about 25 nm, such as at most about 20 nm, such as at most about 10 nm, such as at most about 5 nm. The upper surface bounding the "surface" region may be any surface of the material, including an external surface or an inner pore surface. Thus, in some embodiments zeolitic materials prepared via the methods described herein have a chemical composition within an upper 5 nm, 10 nm, 20 nm, or 25 nm region that differs, at least with respect to the relative amounts of silicon, aluminum, and/or phosphorous, from the chemical composition of the unmodified zeolitic material within the same depth range.

As used herein, modifying a crystal structure of a zeolitic material includes the selective decomposition of intermingled and/or intergrown AEI and/or AFI framework impurity from the crystal structure of a zeolitic material. As will be appreciated by those of skill in the art, in excess of 200 framework types are known for zeolitic materials, and each unique framework type is assigned a 3-letter code by the Structure Commission of the IZA that is recognized by the IUPAC. In some embodiments, it is preferable for zeolitic materials to have the CHA framework type. However, synthesis of certain zeolitic materials with this framework type is often difficult without intermingling and/or intergrowing the less desirable AEI and/or AFI framework as an impurity. In some embodiments, zeolitic materials having the CHA framework with intermingled and/or intergrown AEI and/or AFI framework impurity may be subjected to methods provided herein to selectively decompose (that is selectively reduce or remove) the intermingled and/or intergrown AEI and/or AFI framework impurity.

As used herein, modifying a crystal or particle size of a zeolitic material includes modifying a physical dimension of the crystal. In some embodiments, modifying the crystal or particle size results in a visual change to the material morphology and shape, often resulting in smaller and thinner crystals with visible holes and surface etching or roughness on the external surface of the material. In some related embodiments, modifying the crystal or particle size results in reduced average crystal or particle size as measured by light scattering, or other methods known within the art.

As used herein, modifying a porosity of a zeolitic material includes modifying one or more characteristics of a zeolitic material that are related to pore distribution. In some embodiments, modifying the porosity of a zeolitic material results in a change in the total pore volume and/or the external pore volume. In some related embodiments, this change is an increase in the total pore volume and/or external pore volume. In some embodiments, modifying the porosity of a zeolitic material may result in a change in the external surface area of the material. In some embodiments, this change is brought about by an increase in total pore volume. In some embodiments, modifying the porosity of a zeolitic material results in a change in the micropore area and/or micropore volume. In some embodiments, modifying the porosity of a zeolite material results in a change to the % porosity as measured by mercury porosimetry. In some embodiments, this change is a decrease in the micropore area and/or micropore volume. In some embodiments, certain characteristics related to pore distribution may remain relatively unchanged, including Brunauer, Emmett, and Teller ("BET") surface area.

In an exemplary embodiment, the methods provided herein comprise providing a pre-synthesized zeolitic starting material and contacting this material with a modifying solution under appropriate conditions to materially modify one or more of a surface composition, crystal structure, crystal or particle size and porosity of the zeolitic material. Various process factors (including ratio of zeolitic starting material to modifying solution, concentration of active constituent(s) in the modifying solution, contact time, and temperature) as well as different modifying solutions, described below, may be selected to accomplish one or more of the modifications described herein.

In some embodiments, a reaction mixture comprising the zeolitic starting material and the modifying solution may be prepared at a ratio of about 1 g to about 50 g zeolitic starting material:about 100 ml modifying solution, such as at a ratio of about 5 g to about 25 g zeolitic starting material, such as at a ratio of about 10 g to about 20 g zeolitic starting material:100 ml modifying solution. In some specific embodiments, the reaction mixture is prepared at a ratio of about 15 g zeolitic starting material:about 100 ml modifying solution. Ratios of zeolite starting material to modifying solution should not be limited to those described above, as scale-up to any desired quantity should be expected to provide similar results.

The selection of ratio of zeolitic starting material to reaction solution combined with various additional process details (including concentration of active constituent(s) in the modifying solution, time of contact, and temperature) may impact the rate and/or extent of modification. Specifically, it has been observed that increasing the concentration of active constituents increases the rate of the modification. In some embodiments, the concentration of active constituents is at least about 0.01 g/ml, such as at least about 0.05 g/ml. In some embodiments, the concentration of active constituents is from about 0.01 g/ml to about 1 g/ml, such as from about 0.05 g/ml to about 0.5 g/ml, such as from about 0.05 g/ml to about 0.3 g/ml. It has additionally been observed that increasing the contact time increases the extent of modification. In some embodiments, the mixture is stirred or mixed for a period of about 30 minutes to about 10 days, such as from about 6 hours to about 10 days, such as from about 12 hours to about 10 days, such as from about 1 day to about 10 days. In some embodiments, the reaction is conducted at a temperature of about room temperature ±25° C., although other embodiments may utilize temperatures above or below this range. In some specific embodiments, the reaction is conducted at about room temperature.

In some embodiments, the methods provided herein may be used to decrease the amount of silicon in a surface of a silicon-containing zeolitic material. As used herein to describe a zeolitic material, the term "silicon-containing" indicates that the zeolitic material comprises a measurable amount, i.e., measurable by an appropriate analytical technique such as ICP, of silicon in the bulk. In some instances, silicon-containing zeolitic materials comprise at least about 0.01 wt. %, such as at least about 0.05 wt. %, such as at least about 0.10 wt. % silicon in the bulk. In some instances, silicon-containing zeolitic materials comprise about 0.01 wt. %, such as at least about 0.05 wt. %, such as at least about 0.10 wt. % to at most about 2.7 wt. %, such as at most about 1.2 wt. %, such as at most about 0.8 wt. %, such as at most about 0.6 wt. % silicon in the bulk.

In some embodiments, the modifying solution is a solution comprising an amine (e.g., methylamine, dimethylamine, trimethylamine, ethylamine, diethylamine, triethylamine, phenylamine, diphenyl amine, etc.). In some embodiments, the modifying solution is a solution comprising an alcoholamine. Exemplary alcoholamines include alcoholamines with varied numbers (e.g., 1, 2, or 3) of alcohol functionalities (e.g. ethanolamine, diethanolamine, triethanolamine, etc), alcoholamines with different chain lengths on the alcohol substituent (e.g. a C1-C4 chain length, e.g., methanolamine, ethanolamine, propanolamine, etc.), and different alkyl substituents on the alcohol amine (e.g. phenyldiethanolamine, N-butyldiethanolamine, 2-N-ethylanilino-ethanol, etc). In some embodiments, the modifying solution is a solution comprising an amino acid (e.g. serine, lysine, phenylalanine). In some embodiments, the modifying solution is an aqueous solution comprising one or more of the above listed components. In some embodiments, the modifying solution is an aqueous synthetic mother-liquor comprising one or more of the above listed components along with additional components typically present in zeolite synthesis mother-liquors following crystallization of the intended product.

In some embodiments, the silicon-containing zeolitic starting material is a SAPO material. In some related embodiments, the SAPO material is SAPO-34, SAPO-56 (AFX structure), SAPO-RHO (RHO-structure), SAPO-18 (AEI structure), SAPO-5 (AFI structure), or mixtures or intergrowth thereof. In some related embodiments, the SAPO starting material is contacted with a modifying solution comprising diethanolamine.

Zeolitic materials with reduced surface silicon content prepared according to the methods described herein have reduced surface silicon content relative to the silicon content of the unmodified zeolitic starting material. As a general statement, silicon-containing zeolitic materials do not have uniform distribution of silicon. Rather, silicon tends to be present at higher concentrations in the uppermost about 20-30 nm of a surface than is typically present in the bulk material. Further, silicon concentration in such materials tends to be highest within the first few nanometers of the surface, with the concentration dropping to a plateau at about 30 nm.

In this regard, the ratio of silicon to aluminum and phosphorous (i.e., S:(Al+P)) of a surface may be determined by any number of conventional methods, for example, surface atomic concentration by X-ray photoelectron spectroscopy (XPS). Zeolitic materials with reduced surface silicon content prepared as described herein have surface ratios of silicon to aluminum and phosphorous that are significantly less than unmodified zeolitic materials. For instance, in a specific exemplary embodiment, an unmodified SAPO-34 starting material having a surface silicon to aluminum and phosphorous ratio of 0.054 (as determined by XPS), may have a surface silicon to aluminum and phosphorous ratio of less than about 0.040, such as less than about 0.035, such as less than about 0.030, such as less than about 0.020 after treatment with a modifying solution comprising diethanolamine.

Further, in some silicon-containing zeolitic materials (including SAPO-34), the ratio of silicon to aluminum and phosphorous within the uppermost about 2-3 nm of the surface is about 1.5× to 2× higher than the same ratio for the bulk material (i.e., at a depth of about 30 nm and beyond). In some embodiments, SAPO-34 materials modified to reduce the amount of surface silicon according to methods provided herein have less variation between the maximum silicon to aluminum and phosphorous ratio and the same ratio in the bulk material. Further, in some embodiments, the drop from maximum to bulk is more gradual, with the plateau for the bulk material occurring at a depth of at least about 40-50 nm from the surface. Thus, in some embodiments, the maximum ratio of silicon to aluminum and phosphorous within the uppermost 2-3 nm of the surface in modified zeolitic materials described herein is about 0.9 to about 1.6 times, such as about 1.2 to about 1.4 times, that of the bulk concentration, with the ratio of silicon to aluminum and phosphorous for the bulk material observable at a depth of about 40 to 50 nm or greater from the surface.

The extent of silicon reduction is also reflected in the wt. % silicon (e.g., as measured by ICP) of a silicon-containing zeolitic material before and after treatment. In one specific exemplary embodiment, an unmodified SAPO-34 starting material having about 1.9 wt. % Si (as determined by ICP), may have about 1.5 wt. % Si after treatment with a modifying solution for reducing silicon, such as a modifying solution comprising diethanolamine Other unmodified SAPO-34 starting materials having more or less wt. % Si may be used to prepare modified SAPO-34 materials with reduced wt. % Si. For instance, in another specific embodiment, an unmodified SAPO-34 starting material having about 0.6 wt. % Si may have about 0.4 wt. % Si after treatment with a modifying solution for reducing silicon, such as a modifying solution comprising diethanolamine. Thus, in some embodiments, the methods described herein may be used to prepare a SAPO-34 material with about 0.4 wt. % to about 2.7 wt. % Si, such as about 0.4 wt. % to about 1.2 wt. % Si, such as about 0.4 wt. % to about 0.8 wt. % Si, such as about 0.4 wt. % to about 0.6 wt. % Si, such as about 0.4 wt. % Si. In another specific embodiment, an unmodified SAPO-18 starting material having about 0.7 wt. % Si may have about 0.4 wt. % Si or less, such as about 0.3 wt. % or less after treatment with a modifying solution for reducing silicon, such as a modifying solution comprising diethanolamine. Thus, in some embodiments, the methods described herein may be used to prepare a SAPO-18 material with about 0.3 wt. % to about 2.7 wt. % Si, such as about 0.3 wt. % to about 1.2 wt. % Si, such as about 0.3 wt. % to about 0.8 wt. % Si, such as about 0.3 wt. % to about 0.6 wt. % Si.

As will be understood, there are a variety of techniques for measuring a crystal and/or particle size characteristic of material. It has been observed that magnified visual inspection (e.g. scanning electron microscopy (SEM)) and light scattering are particularly useful techniques for characterizing changes in crystal and/or particle size as well as crystal morphology or topology in a zeolitic material subjected to the methods provided herein. For instance, when the methods described above are used to reduce the crystal or particle size in silicon-containing zeolitic material, it has been observed that the crystal or particle size of the material (as measured by light scattering) decreases linearly with the extent of silicon reduction (as measured by reduction in bulk wt. % of Si of the product following treatment in the modifying solution). Thus, in some embodiments, a modified silicon-containing zeolitic material (such as a modified SAPO-34 or SAPO-18 material) may be obtained with an average crystal or particle size of about 700 nm and a Si-content of about 1.5 wt. % when starting with an unmodified zeolite material of average crystal or particle size of about 1000 nm and a Si-content of about 1.9 wt. %. In some related embodiments, visual changes in the material morphology and topology can be observed following treatment with a modifying solution.

As will be understood, there are a variety of techniques for measuring a porosity characteristic of material. It has been observed that mercury porosimetry is a particularly useful technique for characterizing changes in porosity or pore distribution in a zeolitic material subjected to the methods provided herein. For instance, when the methods described above are used to reduce the amount of silicon in silicon-containing zeolitic material, it has been observed that the % porosity of the material (as measured by mercury porosimetry) increases with the extent of silicon reduction (as measured by reduction in bulk wt. % Si in the material following treatment with a modifying solution). Thus, in some embodiments, a modified silicon-containing zeolitic material (such as a modified SAPO-34 or SAPO-18 material) has a % porosity (as measured by mercury porosimetry) of greater than about 65%, such as about 65% to about 80%, such as about 70% to about 80%, such as about 75% to about 80%.

Additionally, in some embodiments, zeolitic materials with reduced surface silicon content prepared according to the methods described herein have no apparent damage to the crystal structure, and minimal, if any, loss in crystallinity (i.e., less than about 10% loss). In some embodiments, modified silicon-containing zeolitic materials prepared as described herein have an average crystal or particle size as measured by light scattering of about 400 nm to about 2500 nm, such as about 500 nm to about 1500 nm, such as about 500 nm to about 1000 nm.

As will be understood, in some embodiments, modified silicon-containing zeolitic materials prepared as provided herein may have two or more of the above described material characteristics (i.e., surface % silicon, surface ratio of silicon to aluminum and phosphorous, decreased silicon concentration gradient with depth, and greater depth at which bulk silicon to aluminum and phosphorous ratio is observed, wt. % silicon as measured by ICP, % porosity as measured by mercury porosimetry, and average crystal or particle size as measured by light scattering). For example, a silicon-containing zeolitic material (such as a SAPO-34 or SAPO-18 material) modified as described herein may have a modified surface silicon content, leading to the more gradual silicon concentration gradient from a surface to the bulk described above combined with a % porosity (as measured by mercury porosimetry) of about 65% to about 80%, such as about 70% to about 80%, such as about 75% to about 80%. In other exemplary embodiments, a silicon-containing zeolitic material (such as a SAPO-34 or SAPO-18 material) modified as described herein may have a % porosity (as measured by mercury porosimetry) of about 65% to about 80%, such as about 70% to about 80%, such as about 75% to about 80%, and an average crystal or particle size (as measured by light scattering) of about 400 nm to about 2500 nm, such as about 500 nm to about 1500 nm, such as about 500 nm to about 1000 nm.

In some embodiments, the methods provided herein may be used to decrease the amount of aluminum and/or phosphorous in a surface of a zeolitic material. In embodiments where decreasing the amount of aluminum and/or phosphorous in the surface is desired, the modifying solution is a solution comprising a halogenated quaternary amine (e.g. tetramethyl ammonium fluoride, tetraethyl ammonium fluoride, tetrapropyl ammonium fluoride, tetramethyl ammonium chloride, tetraethyl ammonium chloride, tetrapropyl ammonium chloride, etc.). In some specific embodiments, the modifying solution is a solution comprising a fluoridated quaternary amine. In some embodiments, the modifying solution is a solution comprising a quaternary ammonium hydroxide and hydrogen fluoride (HF). In some embodiments, the modifying solution is an aqueous solution comprising one or more of the above listed components. In some embodiments, the modifying solution is an aqueous synthetic mother-liquor comprising one or more of the above listed components along with additional components typically present in zeolite synthesis mother-liquors following crystallization of the intended product.

As above with silicon reduction, zeolitic materials with reduced aluminum and/or phosphorous content in the surface prepared according to the methods described herein have reduced aluminum and/or phosphorous content in the surface relative to the aluminum and/or phosphorous content in the surface of the unmodified zeolitic starting material. Further, in some embodiments, the modified zeolitic materials additionally have increased silicon content relative to the unmodified zeolitic starting material. In some embodiments, zeolitic materials treated to reduce aluminum and/or phosphorous content may include SAPO materials (including SAPO-34 materials), MeAPSO materials, ALPO materials, MeAPO materials, aluminosilicate zeolites, and metal-substituted aluminosilicate zeolites.

In some embodiments, the modifying solution further comprises a silicon source. In some of these embodiments, treating a zeolitic material according to the methods provided herein reduces aluminum and/or phosphorous in the surface while increasing silicon.

In some embodiments, a SAPO-34 material may be treated to reduce aluminum and/or phosphorous (and/or increase silicon content) in the surface. The resulting modified SAPO-34 materials may be particularly suitable for use as catalysts where elevated acid site density or acid strength is desired (e.g., olefin oligomerization, methanol to aromatics conversion, etc.).

In some embodiments, an ALPO material may be treated to reduce aluminum and/or phosphorous (and introduce silicon content) in the surface. In such embodiments, the methods provide synthesis routes to SAPOstructures by transformation of a previously synthesized ALPO to a SAPO.

Similarly, in some embodiments, a MeAPO material may be treated to reduce aluminum and/or phosphorous (and introduce silicon content) in the surface. In such embodiments, the methods provide synthesis routes to MeAPSO structures by transformation of a previously synthesized MeAPO to a MeAPSO.

In some embodiments, aluminosilicate zeolites (such as SSZ-13 (chabazite), pentasil family, etc.) may be treated to reduce aluminum (and/or increase silicon content). In such embodiments, the resulting modified alminosilicate zeolites may have improved suitability for methanol-to-hydrocarbon catalysis, such as methanol-to-propylene catalysis and olefin methylation.

The extent of aluminum and/or phosphorous reduction in the surface is reflected in the wt. % (as measured by ICP) before and after treatment. In one specific exemplary embodiment, an unmodified SAPO-34 starting material with about 1.7 wt. % Si, 22.3 wt. % Al, and 21.7 wt. % P (as determined by ICP), was treated with a modifying solution comprising a silicon source and tetraethyl ammonium fluoride (TEAF). The resulting SAPO-34 material had about 7.3 wt. % Si, 20.8 wt. % Al, and 17.2 wt. % P. Thus, in some embodiments, the methods described herein may be used to prepare a SAPO-34 material with about 7.3 wt. % Si or more, 20.8 wt. % Al or less, and/or about 17.2 wt. % P or less.

In some embodiments, the methods provided herein may be used to decrease the amount of intermingled and/or intergrown AEI and/or AFI framework impurity present in a zeolitic material having the CHA framework. That is, it has surprisingly been found that treatment with certain modification solutions results in selective decomposition of zeolitic materials with the AEI and/or AFI framework, particularly if the AEI and/or AFI framework material is an impurity intermingled and/or intergrown with a zeolitic material with the CHA framework. In embodiments where reduction of the amount of intermingled and/or intergrown AEI and/or AFI framework impurity present in a zeolitic material having the CHA framework is desired, the modifying solution is a solution comprising a halogenated quaternary amine (e.g. tetramethyl ammonium fluoride, tetraethyl ammonium fluoride, tetrapropyl ammonium fluoride, tetramethyl ammonium chloride, tetraethyl ammonium chloride, tetrapropyl ammonium chloride, etc.). In some specific embodiments, the modifying solution is a solution comprising a fluoridated quaternary amine. In some embodiments, the modifying solution is a solution comprising a quaternary ammonium hydroxide and hydrogen fluoride (HF). In some embodiments, the modifying solution is an aqueous solution comprising one or more of the above listed components. In some embodiments, the modifying solution is an aqueous synthetic mother-liquor comprising one or more of the above listed components along with additional components typically present in zeolite synthesis mother-liquors following crystallization of the intended product.

In one exemplary embodiment, the amount of intermingled and/or intergrown AEI framework impurity in a SAPO-34 material was reduced from approximately 40% AEI to about 33% AEI after treatment with a modifying solution comprising tetraethyl ammonium fluoride. In other embodiments, the amount of intermingled and/or intergrown AEI framework impurity in a treated SAPO-34 material may be less than or equal to about 30%, such as less than or equal to about 20%, such as less than or equal to about 10%, based on the total weight of all components in the treated SAPO-34 material.

In some embodiments, the methods provided herein may be used to modify one or more characteristics of a zeolitic material related to crystal or particle size and crystal morphology or topology. It has been observed that magnified visual inspection (e.g. SEM) and light scattering are particularly useful techniques for characterizing changes in crystal and particle size as well as crystal morphology or topology in a zeolitic material subjected to the methods provided herein. For instance, when the methods described above are used to reduce the crystal or particle size in a zeolitic material, it has been observed that the crystal or particle size of the material (as measured by light scattering) decreases with the effectiveness of the treatment (as measured by total yield loss across the treatment step). Thus in some embodiments, a decrease in average crystal or particle size may be achieved. In some embodiments, alterations to the external crystal morphology and topology may be observed following treatment in the modifying solution.

In some embodiments, the methods provided herein may be used to modify one or more characteristics of a zeolitic material related to porosity and pore distribution. For instance, in some embodiments, a zeolitic material may be contacted with a modifying solution to increase the total pore volume and/or the external pore volume. In some embodiments, the pore volume from pores with an average dimension of about 10-18 nm and/or about 30-100 nm is increased. In some embodiments, an increase in total pore volume and/or external pore volume is accompanied with an increase in the external surface area of the material. In some embodiments, the % porosity (as measured by mercury porosimetry) of a treated zeolitic material increases relative to the starting zeolitic material. In some embodiments, the BET surface area and micropore area and/or micropore volume of the treated zeolitic material is decreased. In some embodiments, one or more characteristics related to pore distribution, such as BET surface area, micropore area and/or volume, and % porosity (as measured by mercury porosimetry), may remain relatively unchanged.

Modifying solutions useful for modifying one or more characteristics of a zeolitic material related to porosity and pore distribution include solutions comprising one or more of the constituents listed above as useful for reducing surface silicon, reducing aluminum and/or phosphorous, and reducing the amount of intermingled and/or intergrown AEI and/or AFI framework impurity. Additionally, modifying solutions useful for modifying one or more characteristics of a zeolitic material related to porosity and pore distribution include solutions comprising a quaternary ammonium hydroxide, including mother-liquor solutions from zeolite synthesis following crystallization of the intended product. Exemplary quaternary ammonium hydroxides include tetramethyl ammonium hydroxide, tetraethyl ammonium hydroxide, tetrapropyl ammonium hydroxide, tetrabutyl ammonium hydroxide, etc.

Surprisingly, it has been found that the counter-ion in modifying solutions comprising a quaternary ammonium compound appears to impact the chemistry of the modifying solution. For instance, as described above, tetraethyl ammonium fluoride acts to selectively remove phosphorous from treated zeolitic materials. However, tetraethyl ammonium hydroxide does not share this selectivity, and instead results in unselective elemental decomposition of the treated zeolitic compound, which in some embodiments, results in modifications to one or more characteristics related to average crystal or particle size, or crystal morphology or porosity, without modification of the relative elemental composition of the material. This class of material modification may be particularly useful when material acid site density is desired to remain unchanged, while material porosity and/or crystal size and/or morphology is desired to be altered.

In some embodiments, treating a zeolitic material with a modifying solution comprising one or more amine, alcoholamine, or amino acid results in reduction of BET surface area, reduction in micropore volume, reduction in total pore volume, increase in external pore volume and external surface area, and increase in % porosity as measured by mercury porosimetry. In some embodiments, treating a zeolitic material with a modifying solution comprising one or more halogenated quaternary amine results in reduction of BET surface area, reduction in micropore volume, reduction in total pore volume, increase in external pore volume and external surface area, and increase in % porosity as measured by mercury porosimetry. In some embodiments, treating a zeolitic material with a modifying solution comprising one or more quaternary amine hydroxides results in little to no change in BET surface area and micropore volume, while increasing external pore volume and external surface area, and increase in % porosity as measured by mercury porosimetry. In an exemplary embodiment, a modified SAPO-34 zeolitic material has one or more of the following characteristics: a micropore surface area of at least about 490 m$^2$/g; an external surface area of at least about 40 m$^2$/g; a total pore volume of at least about 0.490 cc/g; a micropore volume of at least about 0.250 cc/g; and an exterior pore volume of at least about 0.240 cc/g.

As will be appreciated, while certain exemplary embodiments described above illustrate the methods provided herein as applied to specific zeolitic materials, it is envisioned that these methods may be applied to any zeolitic material having any crystal framework type, without limit, to yield a zeolitic materials with modified surface composition, crystal properties, and/or porosity. Further, modifying solutions may be used which comprise any combination of the above described agents, without limit. In this way, it is possible for a modifying solution to be used to achieve a plurality of the above described effects. For instance, a modifying solution comprising diethanolamine and tetraethyl ammonium fluoride may be used reduce crystal size and surface silicon while simultaneously reducing an amount of intermingled and/or intergrown AEI framework impurity. Thus, in some embodiments, modified zeolitic materials may be prepared in which a plurality of the above described characteristics have been modified. In a particular exemplary embodiment, a modified SAPO-34 material may be prepared according to methods described herein that has low silicon content (e.g., 0.4-3.0 wt. %, such as 0.4-2 wt. %, such as 0.4-1.2 wt. %) and low AEI (e.g., less than about 20 wt. %, such as less than about 10 wt. %). Such materials may additionally have beneficial modifications to their crystal or particle size (which improves mass transport properties and thus provide improvements to catalytic performance), crystal morphology or topology, pore structure, including increases in external surface area, external pore volume, and % porosity (which improve mass transport properties of the material, and thus provide improvements to catalytic performance), without significantly adversely affecting micropore surface area or micropore volume.

As indicated above, it is intended that modified zeolitic materials prepared according to methods described herein may be used as catalytic materials. In some particular embodiments, modified SAPO materials prepared as described above may be employed as catalysts to convert oxygenates to olefins. As will be appreciated, the term oxygenate is used to describe organic compounds with oxygen in their chemical structure. Exemplary oxygenates include alcohols, aldehydes and ethers. The term olefin is used to describe unsaturated hydrocarbons with at least one carbon-carbon double bond. In a particular embodiment, modified SAPO materials prepared as described above may be employed as catalysts for the conversion of methanol to olefins (MTO).

Thus, in another aspect, methods of converting an oxygenate to an olefin via a SAPO catalyzed reaction are provided. In these methods, a feed stream comprising an oxygenate such as methanol, formaldehyde or dimethyl ether is contacted with a catalyst comprising at least one modified SAPO material as described herein under conditions suitable for conversion of an oxygenate to an olefin. In some embodiments, the oxygenate is methanol and/or dimethyl ether, and the olefin is ethylene and/or propylene. Conditions employed to use the catalysts in an oxygenate-to-olefin conversion reaction can be readily identified by a person of ordinary skill in the art. In an exemplary embodiment, a modified SAPO material may be a modified SAPO-34 material.

In an exemplary embodiment, a modified SAPO material as described herein may be sized by a 40/60 standard mesh, and a portion of the sized material placed in a fixed bed reactor. In one specific example, the reactor is heated to a temperature of about 450° C. and a methanol and/or dimethyl ether-comprising feed is introduced to the reactor at a pressure of about 72 psig ($P_{MeOH}$ ~40 psig). A reactor effluent comprising light olefins including ethylene and propylene is generated via catalytic conversion.

When used to catalyze MTO conversion, modified SAPO-34 materials prepared as described herein to have reduced surface silicon content display increased light olefin (i.e., ethylene and propylene) production and decreased heavy olefin (i.e., olefins heavier than propylene) production relative to unmodified SAPO-34 catalysts. Further, the modified SAPO-34 materials exhibit different ethylene and propylene selectivity profiles as compared to unmodified SAPO-34 catalysts. In particular, SAPO-34 catalysts with reduced surface silicon exhibit increased selectivity for both ethylene and propylene at early TOS as compared to selectivities observed for unmodified SAPO-34 materials. In some embodiments, after a length of time, the advantage in ethylene selectivity of SAPO-34 catalysts with reduced surface silicon over untreated SAPO-34 catalysts is reduced, however, the propylene selectivity advantage continues until catalyst failure. In some embodiments, the modified SAPO-34 materials exhibit reduced selectivities for propane and reduced generation and accumulation of carbonaceous materials (i.e., coke) in and on the catalyst.

Also described herein are systems for using modified zeolitic materials prepared according to methods described herein as catalyst materials. In a particular embodiment, systems are described for converting an oxygenate to an olefin in a SAPO catalyzed reaction. The following exemplary systems are described with reference to the attached FIGURE. Exemplary systems include a reaction vessel 2 configured to contain one or more catalytically active modified zeolitic materials 4 prepared according to methods described herein. In a particular embodiment, the reaction vessel 2 is configured to receive a oxygenate-containing feed stream 6, and contact the feed stream 6 with a catalytically active modified SAPO 4 under reaction conditions effective to convert an oxygenate to an olefin and produce an olefin-containing effluent 8. In some embodiments, the feed stream 6 comprises one or more of methanol and dimethyl ether. In these embodiments, the olefin-containing effluent 8 comprises one or more of propylene and ethylene.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for reducing a surface silicon content of a silicon-containing zeolitic material, the method comprising the steps of: providing a zeolitic material comprising silicon at a surface of the zeolitic material; and
   contacting the surface of the zeolitic material with a modifying solution comprising one or more of an amine, or an alcoholamine,
   wherein contacting the surface of the zeolitic material with the modifying solution reduces an amount of silicon at the surface to generate a modified zeolitic material with a reduced surface silicon content and wherein contacting the surface of the zeolitic material with a modifying solution comprises contacting the surface of the zeolitic material with an alcoholamine with one, two or three alcohol functionalities, a C1 to C4 chain length on an alcohol substituent, or both, or contacting the surface of the zeolitic material with a modifying solution comprises contacting the surface of the zeolitic material with a diethanolamine, or a combination thereof.

2. The method of claim 1, wherein providing a zeolitic material comprises providing a silicoaluminophosphate (SAPO), a metal-substituted silicoaluminumphosphate (MeAPSO), or a combination thereof.

3. The method of claim 1, wherein providing a zeolitic material comprises providing a metal-substituted silicoaluminumphosphate (MeAPSO) comprising one or more metals from groups 2 through 13 of the periodic table of elements.

4. The method of claim 1, wherein providing a zeolitic material comprises providing a metal-substituted silicoaluminumphosphate (MeAPSO) comprising magnesium (Mg), calcium (Ca), scandium (Sc), titanium (Ti), vanadium (V), chromium (Cr), manganese (Mn), iron (Fe), cobalt (Co), nickel (Ni), copper (Cu), zinc (Zn), gallium (Ga), or a combination thereof.

5. The method of claim 1, wherein contacting the surface of the zeolitic material with a modifying solution comprises contacting the surface of the zeolitic material with one or more of methylamine, dimethylamine, trimethylamine, ethylamine, diethylamine, triethylamine, phenylamine, and diphenyl amine.

6. The method of claim 1, wherein providing a zeolitic material comprises providing a SAPO-34 material and wherein the method produces a modified SAPO-34 material with a bulk silicon content of about 0.4 wt. % and 2.7 wt. % Si.

7. The method of claim 1, wherein providing the zeolitic material comprises providing a SAPO-18 material and wherein the method produces a modified SAPO-18 material with a bulk silicon content of about 0.3 wt. % and 2.7 wt. % Si.

8. The method of claim 1, wherein the zeolitic material comprises a silicoaluminophosphate (SAPO), a metal-substituted silicoaluminumphosphate (MeAPSO), or a combination thereof; and
   wherein reducing the surface silicon content of the zeolitic material comprises reducing the silicon:(aluminum+phosphorous) ratio at the surface of the silicon-containing zeolitic material.

9. The method of claim 1, wherein contacting the surface of the zeolitic material with the modifying solution additionally increases the % porosity, decreases the average crystal or particle size, or both, to generate a modified zeolitic material with a reduced surface silicon content and elevated % porosity, decreased crystal size, or both.

10. The method of claim 1, wherein the zeolitic material comprises SAPO-34, metal-substituted SAPO-34, SAPO-18, metal-substituted SAPO-18, SAPO-56, SAPO-RHO, SAPO-5, or mixtures or intergrowths thereof.

11. A method for reducing a surface silicon content of a silicon-containing zeolitic material, the method comprising the steps of:
    providing a zeolitic material comprising silicon at a surface of the zeolitic material, wherein the zeolitic material comprises a silico-alumino-phosphate (SAPO), a metal-substituted silicoaluminumphosphate (MeAPSO), or combinations thereof, wherein the zeolitic material comprises SAPO-34, metal-substituted SAPO-34, SAPO-18, metal-substituted SAPO-18, SAPO-56, SAPO-RHO, SAPO-5, or mixtures or intergrowths thereof; and
contacting the surface of the zeolitic material with a modifying solution comprising one or more of an amine, or an alcoholamine, an alcoholamine with one, two, or three alcohol functionalities, a C1 to C4 chain length on an alcohol substituent, or both or wherein contacting the surface of the zeolitic material with a modifying solution comprises contacting the surface of the zeolitic material with a diethanolamine, or a combination thereof. wherein contacting the surface of the zeolitic material with the modifying solution reduces an amount of silicon at the surface to generate a modified zeolitic material with a reduced surface silicon content.

12. The method of claim 11, wherein providing a zeolitic material comprises providing a metal-substituted silicoaluminumphosphate (MeAPSO) comprising one or more metals from groups 2 through 13 of the periodic table of elements.

13. The method of claim 11, wherein the modifying solution has a concentration of active constituents of from about 0.01 g/ml to about 1 g/ml, or wherein a ratio of the zeolitic material to the modifying solution is about 1 to about 50 g zeolitic material:100 ml of modifying solution, or both.

* * * * *